(12) United States Patent
Kramer et al.

(10) Patent No.: US 10,246,724 B2
(45) Date of Patent: Apr. 2, 2019

(54) PRODUCTION OF HYDROGEN USING AN ANAEROBIC BIOLOGICAL PROCESS

(71) Applicant: Purdue Research Foundation, West Lafayette, IN (US)

(72) Inventors: Robert Kramer, Crown Point, IN (US); Libbie S. Pelter, Schereville, IN (US); John A. Patterson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/358,008

(22) Filed: Nov. 21, 2016

(65) Prior Publication Data
US 2017/0211033 A1     Jul. 27, 2017

Related U.S. Application Data

(62) Division of application No. 13/891,435, filed on May 10, 2013, now Pat. No. 9,506,084.

(60) Provisional application No. 61/645,325, filed on May 10, 2012.

(51) Int. Cl.
| | |
|---|---|
| *C12P 13/00* | (2006.01) |
| *F03G 6/00* | (2006.01) |
| *C12M 1/107* | (2006.01) |
| *C02F 11/04* | (2006.01) |
| *C12P 3/00* | (2006.01) |

(Continued)

(52) U.S. Cl.
CPC ............... *C12P 3/00* (2013.01); *C12M 21/04* (2013.01); *C12M 43/00* (2013.01); *C12M 43/08* (2013.01); *C12P 7/06* (2013.01); *F03G 6/00* (2013.01); *C02F 11/04* (2013.01); *C02F 2303/10* (2013.01); *H01M 2250/40* (2013.01); *Y02E 50/17* (2013.01); *Y02E 50/343* (2013.01); *Y02E 60/56* (2013.01); *Y02W 10/30* (2015.05); *Y02W 10/37* (2015.05)

(58) Field of Classification Search
CPC ..... C12P 3/00; C12P 7/06; F03G 6/00; C12M 43/08; C12M 43/00; C12M 21/04; Y02W 10/30; Y02W 10/37; Y02E 60/56; Y02E 50/343; Y02E 50/17; C02F 11/04; C02F 2303/10; H01M 2250/40
USPC ................ 60/641.8–641.15; 435/168, 289.1; 48/127.7
See application file for complete search history.

(56) References Cited

U.S. PATENT DOCUMENTS 6,368,849 B1 *  4/2002  Norddahl .............. C02F 3/2853
                                                                210/603
9,506,084 B2 * 11/2016  Kramer .................... C12P 3/00
(Continued)

OTHER PUBLICATIONS

Kramer, Robert A., et al., "Production of Hydrogen Using an Anaerobic Biological Process," World Energy Eneginering Congress Proceedings, 2011. Dec. 31, 2011.
(Continued)

*Primary Examiner* — Hoang M Nguyen
(74) *Attorney, Agent, or Firm* — Brian W. Chellgren; Bingham Greenbaum Doll LLP (57) ABSTRACT

Various embodiments of the present invention pertain to methods for biological production of hydrogen. More specifically, embodiments of the present invention pertain to a modular energy system and related methods for producing hydrogen using organic waste as a feed stock.

15 Claims, 9 Drawing Sheets

(51) Int. Cl.
*C12M 1/00* (2006.01)
*C12P 7/06* (2006.01)

(56) References Cited

U.S. PATENT DOCUMENTS

| 2007/0082387 A1* | 4/2007 | Felder ........................ C02F 3/34 |
| | | 435/168 |
| 2007/0157614 A1* | 7/2007 | Goldman .................. F02C 3/22 |
| | | 60/641.15 |
| 2012/0060418 A1* | 3/2012 | Epstein .................. B01J 23/462 |
| | | 48/127.7 |

OTHER PUBLICATIONS

Kramer, Robert., et al. "Modular Waste/Renewal Energy System for Production of Electricity, Heat and Potable Water in Remote Locations," IEEE Humanitarian Technology Conference Proceedings, 2011. Dec. 31, 2011.

Kramer, Robert, et al., "Utilization of Solar Heat to Process Organic Wastes for Biological Hydrogen Production," Energy Engineering, vol. 108, No. 3, Apr.-May 2011. May 31, 2011.

* cited by examiner

PRODUCTION OF HYDROGEN USING AN ANAEROBIC BIOLOGICAL PROCESS

CROSS REFERENCE TO RELATED APPLICATION

This application is a divisional of U.S. Non-Provisional patent application Ser. No. 13/891,435, filed May 10, 2013, entitled PRODUCTION OF HYDROGEN USING AN ANAEROBIC BIOLOGICAL PROCESS, which claims the benefit of priority to U.S. Provisional Patent Application Ser. No. 61/645,325, filed May 10, 2012, entitled PRODUCTION OF HYDROGEN USING AN ANAEROBIC BIOLOGICAL PROCESS, both of which are incorporated herein by reference.

GOVERNMENT RIGHTS

This invention was made with government support under DE-FG36-06GO86050 awarded by the Department of Energy. The government has certain rights in the invention.

FIELD OF THE INVENTION

Various embodiments of the present invention pertain to methods for biological production of hydrogen. More specifically, embodiments of the present invention pertain to a modular energy system and related methods for producing hydrogen using organic waste and agricultural byproducts as a feed stock.

BACKGROUND OF THE INVENTION

Production of hydrogen by biological processes is potentially a renewable source of energy. Using organic wastes and agricultural byproducts for bioproduction of hydrogen has the potential to generate cost effective and renewable energy and also can reduce pollution in the environment and provide a source of crop fertilizer.

Large quantities of ethanol are produced for use as a transportation fuel. When grain is used in this process, the material remaining after ethanol has been produced is referred to as Dry Distillers Grain Plus Solubles ("DDGS"). This agricultural byproduct is often used as animal feed for cattle and other animals. As use of ethanol increases, the supply of DDGS outstrips the demand for the product as animal feed. A need exists for an alternative use of DDGS and organic wastes.

SUMMARY OF THE INVENTION

Various embodiments of the present invention pertain to the biological production of hydrogen from organic wastes and agricultural byproducts, including use of that hydrogen to generate electricity in modular energy systems. For simplicity, traditional organic wastes such as food waste, human waste, animal waste, and garbage, and agricultural byproducts such as DDGS are collectively referred to organic wastes. Biological production of hydrogen gas offers a sustainable method for the production of fuel with a concurrent minimization of waste. Unlike fossil fuels, combustion of hydrogen does not produce carbon dioxide or sulfur oxides. Hydrogen also has a higher energy yield (120 kJ/g) than hydrocarbons (44 kJ/g, petroleum). Conventional chemical methods for hydrogen production are energy intensive. Biological hydrogen (biohydrogen) production methods utilizing microorganisms potentially offer an economically feasible and sustainable alternative for producing hydrogen.

The present invention may generate renewable energy from organic waste and reduce pollution. In certain embodiments, the present invention pertains to production of hydrogen, and at least one of heat, potable water, and sanitized fertilizer from anaerobic fermentation of organic waste. In some embodiments, the organic wastes are food waste streams and DDGS. Food waste includes waste from consumption of food and waste from processing food, such as, for example, soybean hulls, wheat hulls, and other plant and animal parts not typically consumed. In further embodiments, the organic wastes further include human wastes, animal wastes, and garbage. In some embodiments, biological production of hydrogen from DDGS increases the efficiency of ethanol production from grain.

One embodiment of the present invention pertains to a method for producing hydrogen including providing an organic waste, fermenting the organic waste in a substantially anaerobic environment, wherein hydrogen is produced from the fermenting, and directing the hydrogen to one of a fuel cell and a heat engine. In further embodiments, the organic waste is one of DDGS, DDG, garbage, human waste, animal waste, and food waste.

In some embodiments, the method further includes heating the organic waste at a temperature effective to substantially sterilize the organic waste, wherein the heating occurs subsequent to the fermenting. In certain embodiments, the fermenting occurs in a bioreactor in proximity to the one of a fuel cell and a heat engine.

In some embodiments, the method further comprises heating the organic waste at a temperature effective to substantially inactivate methane-producing microorganisms, wherein the heating occurs prior to the fermenting.

In further embodiments, the method further comprises heating an inoculum at a temperature effective to substantially inactivate methane-producing microorganisms, but ineffective to substantially inactivate hydrogen-producing microorganisms, and adding the inoculum to the organic waste, wherein the heating occurs prior to the adding, and wherein the adding occurs prior to the fermenting. In certain embodiments, carbon dioxide is produced from the fermenting.

In some embodiments, the method further comprises separating the hydrogen from the carbon dioxide prior to the directing. In further embodiments, the fermenting occurs at a pH between about 4.5 and about 6.5.

Another embodiment of the present invention pertains to a method for producing hydrogen including heating an organic waste at a temperature effective to substantially inactivate methane-producing microorganisms, heating an inoculum at a temperature effective to substantially inactivate methane-producing microorganisms, but ineffective to substantially inactivate hydrogen-producing microorganisms, and fermenting the organic waste and inoculum in a bioreactor, wherein hydrogen is produced from the fermenting. In some embodiments, the organic waste is one of garbage, human waste, animal waste, and food waste. In further embodiments, the heating the organic waste is heating the organic waste at a temperature of at least 90° C. In certain embodiments, the heating the inoculum is heating the inoculum at a temperature between about 90° C. and about 100° C. In some embodiments, the inoculum includes microorganisms competent to produce hydrogen from fermentation of organic waste. In further embodiments, the fermenting occurs at a pH between about 4.5 and about 6.5.

A further embodiment of the present invention pertains to a method for producing renewable fuel from grains including producing ethanol and DDGS from grains, and fermenting the DDGS in a substantially anaerobic environment to produce hydrogen gas.

Another embodiment of the present invention pertains to a modular renewable energy system including a solar collector system for generating heat energy, a bioreactor including a chamber for fermenting organic waste, and one of a fuel cell and a heat engine in gaseous communication with the bioreactor, wherein anaerobic fermentation of organic waste in the chamber generates hydrogen gas, the hydrogen gas being directed to the one of a fuel cell and a heat engine.

In some embodiments, the modular renewable energy system further includes a housing having an interior and an exterior, wherein the bioreactor is located in the interior of the housing, the one of a fuel cell and a heat engine is located in the interior of the housing, and the solar collector system is located on the exterior of the housing. In further embodiments, heat energy effective to substantially inactivate methane-producing microorganisms is applied to the organic waste prior to fermentation, the heat energy being generated by the solar collector system. In certain embodiments, heat energy effective for sterilization is applied to the organic waste subsequent to fermentation, the heat energy being generated by the solar collector system.

In further embodiments, the modular renewable energy system further includes an apparatus for distilling water using heat energy generated by the solar collector system. In certain embodiments, the modular renewable energy system further includes a controller for controlling the temperature and pH within the bioreactor chamber.

In some embodiments, the heat engine combusts the hydrogen in a cylinder to drive a piston. In further embodiments, the heat engine combusts the hydrogen in the combustor of a gas turbine. In certain embodiments, the one of a fuel cell and a heat engine is located proximate to the bioreactor. In some embodiments, the solar collector system is located proximate to the bioreactor.

In further embodiments, the modular renewable energy system further includes a gas conditioner for separating hydrogen from other gases, wherein hydrogen is directed to the gas conditioner prior to being directed to the one of a fuel cell and a heat engine.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is excessive and unnecessary.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

The use of an N-series prefix for an element number (NXX.XX) refers to an element that is the same as the non-prefixed element (XX.XX), except as shown and described thereafter. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only. Further, with discussion pertaining to a specific composition of matter, that description is by example only, and does not limit the applicability of other species of that composition, nor does it limit the applicability of other compositions unrelated to the cited composition.

The present disclosure describes production of hydrogen from various waste streams using microbial fermentation and implementation of the technology as an energy source. The present disclosure also describes acceptable and preferred growth conditions for hydrogen production. The hydrogen will be purified and used to produce electricity by means of either a fuel cell and/or a heat engine, such as a reciprocating engine/generator. An energy balance model for the proposed system has been developed as part of the optimization process. This model simulates hydrogen production rates, electric production, and thermal energy balances for different design options for the proposed modular energy system.

The present disclosure describes embodiments of a modular energy system for the bioproduction of hydrogen from organic wastes. This modular energy system utilizes waste products to generate useful hydrogen gas, a renewable energy source. In further embodiments, the system utilizes anaerobic fermentation of organic waste to produce hydrogen, heat, potable water, and sanitized fertilizer. Organic wastes include food waste streams, DDGS, Dry Distillers Grain ("DDG"), human wastes, animal wastes, and garbage. The produced hydrogen may be directed for use in a fuel cell or heat engine, such as a reciprocating engine, to supply electricity locally. The modular energy system is particularly well adapted to provide electricity at remote locations, as the feed material for the system is local waste material and hence it does not have issues with the logistics of fuel transportation as do many other conventional energy sources. In this application, the modular energy system has added value for waste processing and heat production as well as local electric production.

The organic waste serving as feed stock for fermentation is preferably heat treated prior to fermentation. The inoculum for the process is also heated to inactivate potential methane-producing microorganisms. For bioproduction processes which have the potential to naturally produce methane, the feed stock is heated to drastically reduce or substantially eliminate methane production. Energy for the preprocessing of feed waste streams is obtained from a solar collector system. In some embodiments, organic waste is heated in a solar based preprocessing unit prior to the organic waste being fermented in a bioreactor.

In some embodiments, the modular energy system is configured for use as a portable, environmentally friendly, energy source useful in remote locations, disaster situations, and other settings. The modular energy system is configured around a transportable housing, such as a conventional shipping container, for ease of manufacture, transportation, and installation. In some embodiments, the housing includes an interior and an exterior with the solar collector system mounted on the exterior of the housing, such as, on the roof of the housing, and the bioreactor is located inside the housing. The preprocessing unit, namely, a chamber capable of being heated by the solar collector system, is also located in the interior of the housing and is in fluid communication with the bioreactor. A screw, fluid transfer mechanism, or other suitable mechanism transfers material from the preprocessing unit to the bioreactor. The fuel cell or heat engine is also located in the interior of the housing, and is in fluid communication with the bioreactor.

Various studies have been conducted using microorganisms to generate hydrogen from fermentation of a variety of substrates. Some studies used single species cultures of bacteria, such as species of *Bacillus, Clostridium*, and *Enterobacter*, while others used mixed cultures that originated from sludge, animal wastes, sewage, compost, soil, etc. Substrates that have been used for fermentation include carbohydrates, such as glucose sucrose, xylose, cellulose, and starch, as well as organic wastes, such as municipal solid waste, starch manufacturing wastes, food processing wastewaters, and food waste. Using organic wastes for bioproduction of hydrogen has the potential to generate cost effective and renewable energy and also can reduce pollution in the environment and provide a source of fertilizer for growing crops.

Figure 1:
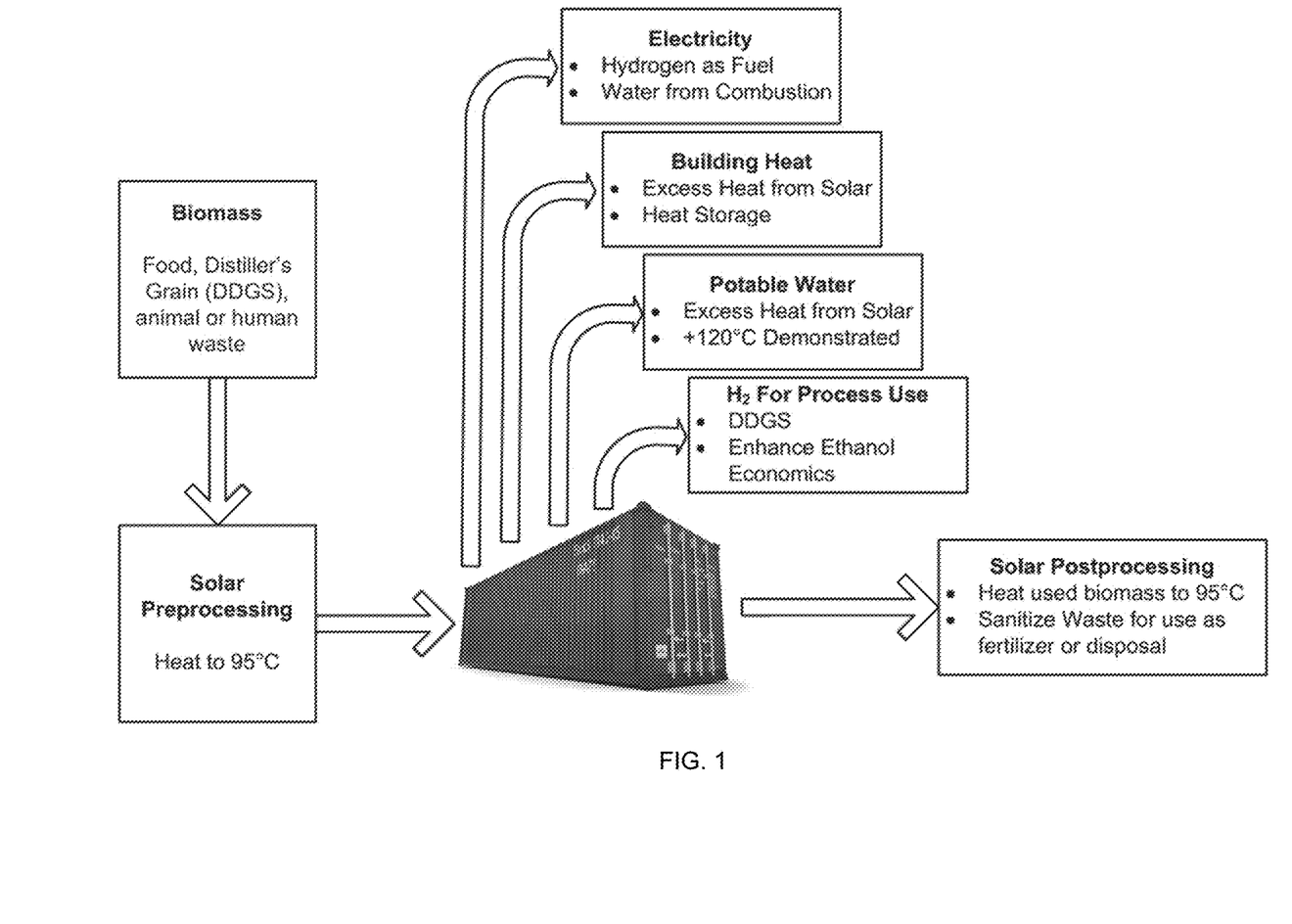
FIG. 1 is a schematic illustrating the inputs and outputs of a modular energy system.

The present disclosure includes a modular distributed energy system based upon the anaerobic fermentation of organic waste to produce hydrogen, thermal energy, potable water, and sanitized fertilizer. It is initially intended for use in remote locations and in disaster situations, although the modular energy system may be used in other situations and locations. It is anticipated that the modular energy system will be housed in standard sized housing, such as, for example, a conventional shipping container, for ease of manufacture, transportation, and installation. The conceptual flow of energy and mass for the modular renewable energy system is depicted in FIG. 1. While this figure indicates that biomass feedstock is heated to 95° C. during preprocessing and post-processing, this temperature should be considered an example and not a limitation. As discussed in further detail below, some embodiments of the modular renewable energy system do not utilize preprocessing heating.

Figure 2:
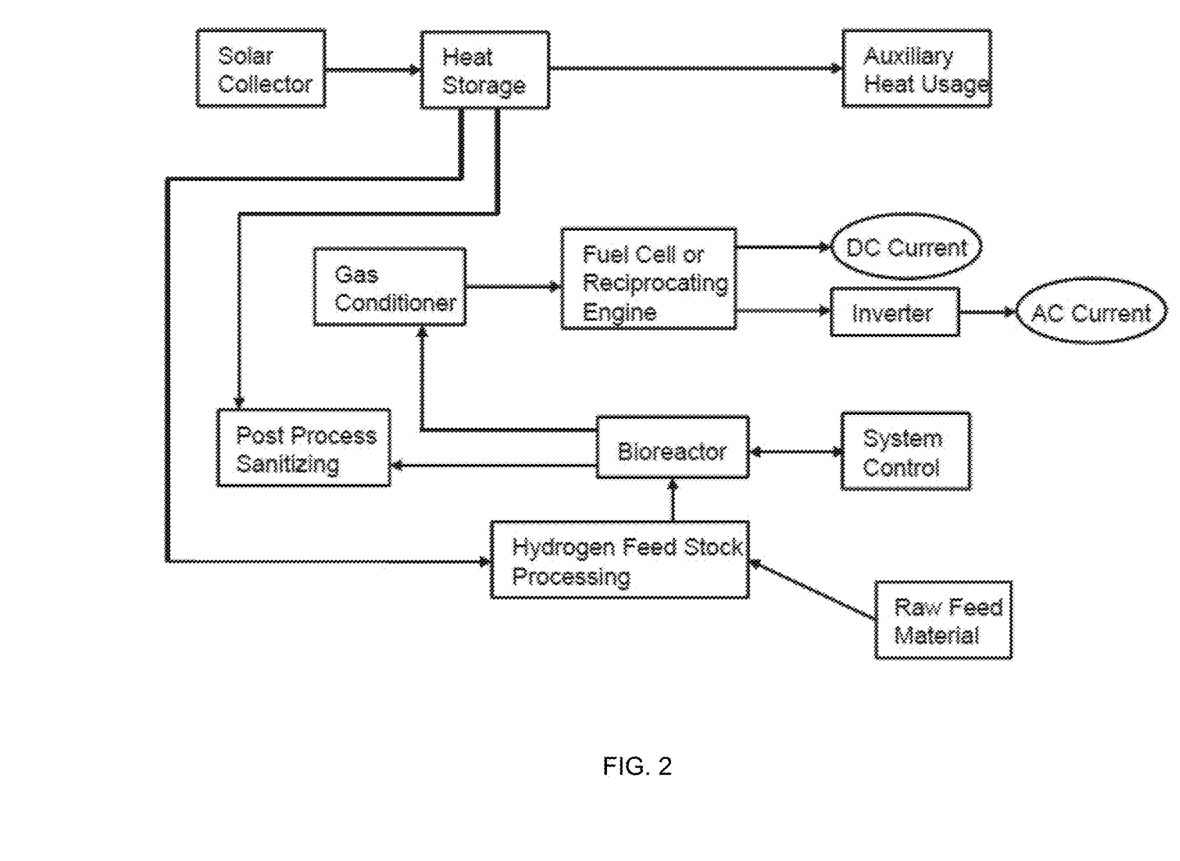
FIG. 2 is a schematic of the modular energy system.

FIG. 2 depicts the modular energy system in further detail. Raw feed material, namely, organic waste, serves as the feed stock for the modular energy system. As preprocessing prior to fermentation, heat energy from the solar collector is applied to the organic waste to inhibit the activity of native microorganisms, particularly methanogens. Organic waste often contains bacteria capable of producing methane, a potent greenhouse gas. Heating the organic waste to inhibit methanogens both decreases the production of a greenhouse gas from the organic waste, and removes bacteria that may compete for resources with preferred hydrogen-producing bacteria. Previous efforts by others have shown that heating the feed material from a municipal sewage treatment plant to 100° C. for 45 minutes inhibits bioactivity of methanogens. The authors have discovered that bioactivity of methanogens can be substantially eliminated by heating organic waste to 95° C. for 15 minutes or to 90° C. for 30 minutes. In some embodiments, temperature of the organic waste in the preprocessing unit is measured by a first thermocouple immersed in the waste and a second thermocouple at the surface of the waste.

Heat treated organic waste is the introduced into the bioreactor, where it is allowed to ferment. The bioreactor includes a controller for controlling the temperature, pH, pressure, water content, and flow rate for the bioreactor. The bioreactor may be a batch or continuous bioreactor. DDGS produced as a byproduct of ethanol production includes hydrogen-producing yeast. For other feed stocks, the organic waste is inoculated with hydrogen-producing microorganisms, then temperature and pH in the bioreactor is controlled to maintain an environment conducive to reproduction of the hydrogen-producing microorganism. In some embodiments, prior to inoculation, the inoculum is heated to a temperature effective to inactivate methane-producing microorganisms, but ineffective to inactivate hydrogen-producing microorganisms. In some embodiments, the hydrogen-producing organism is *Clostridium. Clostridium* is capable of surviving exposure to a temperature of 100° C., which is higher than the temperature used to substantially inactivate methane-producing microorganisms. In other embodiments, other hydrogen-producing microorganisms or combination of hydrogen-producing microorganisms may be used.

Fermentation results in the bioproduction of hydrogen, which is directed to a gas conditioner to separate hydrogen gas from nitrogen, carbon dioxide, and other contaminants. The hydrogen gas is then directed to a fuel cell or heat engine, such as a reciprocating engine, to produce electricity. The fuel cell or heat engine may produce direct current ("DC") or, through use of an inverter, alternating current ("AC") power.

After fermentation, a post-processing heat treatment is applied to the organic waste to sterilize the material. The waste is directed to a post-processing unit in fluid communication with the bioreactor. In some embodiments, the post-processing unit is a tank in the interior of the housing, which is heated using heat energy from the solar collector.

The waste is heated to at least 85° C. for 30 minutes or, in other embodiments, to at least 95° C. for 30 minutes. The sterilized organic waste may then be used as fertilizer or put to other use.

Heat generated by the solar collector may be stored in a thermal storage unit. Stored heat can be put to auxiliary uses apart from heat treatment of organic waste. For example, heat generated from the solar collector may be applied to a distillation apparatus containing non-potable water to distill potable water. The generated heat may also be used to heat or assist in heating buildings or other facilities in proximity to the modular energy system.

The modular energy system employing a vacuum tube solar collector (Apricus Solar Co., Ltd, 20 and 22 tube vacuum tube solar collectors in series) routinely produces temperatures of 120° C., produces multiple products and associated value streams including: hydrogen for production of electricity, waste disposal, heat for buildings, drinking water, fertilizer, and marketable chemical product produced from process carbon dioxide, such as, for example, carboxylic acids, amides, polymers, or produced carbon dioxide could be directed to a greenhouse to enhance plant growth. It has been possible to distill water using this solar collector system and thereby produce potable water. In some embodiments, non-potable water is added to a distillation apparatus, the apparatus heated by heat energy from the solar collector, and potable water distilled. In other embodiments, water derived from the organic waste is directed into the distillation apparatus for distillation.

Figure 3:
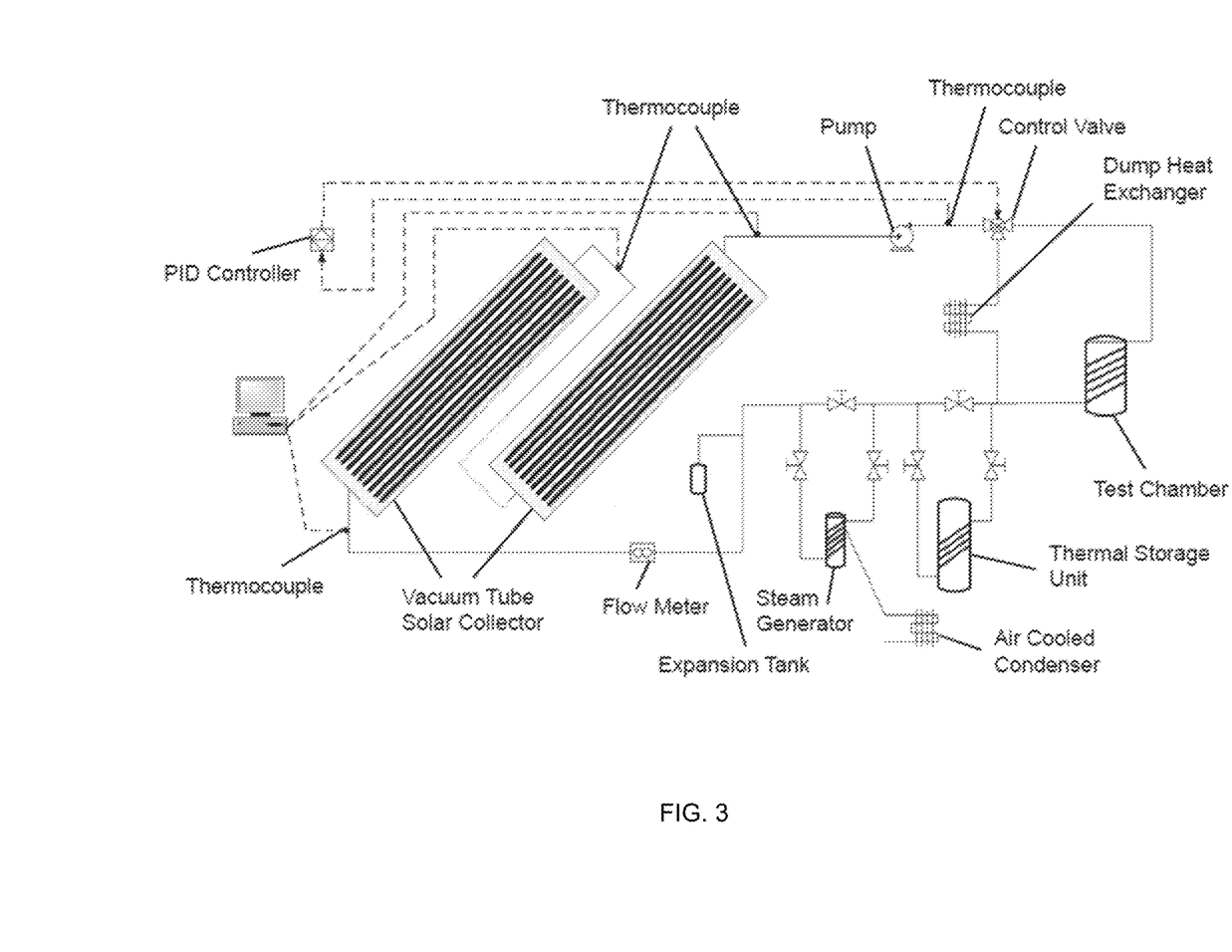
FIG. 3 is a schematic of a solar collector system.

FIG. 3 depicts an exemplary solar collector, in which liquid flows through and is heated in vacuum tube solar collectors. The liquid is directed through a closed system via a pump and can be used to generate steam, which can be directed to other components of the modular energy system to provide useful heat energy. Heat energy may be stored in a thermal storage unit, such as, for example, by heating water in an insulated storage tank, by storing heat energy in a phase change material, or by other suitable methods of storing heat energy.

The rate of production and final quantity of hydrogen produced by the anaerobic process is a function of the operating conditions. Various combinations of substrate concentration, initial pH, and temperature were considered in a central composite experimental design to understand their influence on hydrogen production.

A computer controlled automated testing device, developed as part of this research effort, was used to simultaneously consider various combinations of operating parameters. This device is an array of specimen bottles that are automatically sampled. The composition of the gas in the headspace of each bottle was measured using a gas chromatograph (GC) (CP-4900 Dual Channel Micro-GC; Varian Inc.) equipped with a thermal conductivity detector and a 10 M-5A molecular sieve column with argon as the carrier gas. Carbon dioxide was measured in the headspace using a separate channel on the same GC equipped with a 10 M Poraplot® (Varian, Inc.) column with helium as the carrier gas. Automated monitoring of the head space gas composition in the individual vials was accomplished using a multi-position stream selection valve (Valco Instruments Co., Inc.) that feeds directly into the injector of the GC as the valve cycles to the individual vials. The quantity of hydrogen produced was then determined based on the volume of gas produced, as determined from pressure data, and the percent hydrogen was determined from the GC. Controlled and/or measured parameters include temperature, residency time, pressure, and pH. The developed device maintains a constant temperature by means of a water bath. Multiple samples, each contained in a 120 mL bottle, can the evaluated simultaneously.

Samples of food waste were collected from a cafeteria at Purdue University in W. Lafayette, Ind. and were inoculated with various types of seed material to test the viability of hydrogen production by anaerobic means. Samples of pig manure were also considered. An analysis of the components of the food waste is depicted in Table I.

TABLE I

FOOD WASTE ANALYSIS

| Component | As Sent | Dry Wt. |
|---|---|---|
| Moisture (%) | 06.30 | ///// |
| Dry Matter (%) | 93.70 | ///// |
| Crude Protein (%) | 17.40 | 18.60 |
| Crude Fat (%) | 12.60 | 13.40 |
| Acid Detergent Fiber (%) | 33.20 | 35.40 |
| Ash (%) | 03.35 | 03.58 |
| Total Digestible Nutrients (%) | 81.50 | 87.00 |
| Net Energy-lactation (Mcal/lb) | 00.85 | 00.91 |
| Net Energy-maint. (Mcal/lb) | 00.90 | 00.96 |
| Net Energy-gain (Mcal/lb) | 00.59 | 00.63 |
| Digestible Energy (Mcal/lb) | 01.63 | 01.74 |
| Metabolizable Energy (Mcal/lb) | 01.51 | 01.61 |
| Sulfur (%) | 00.26 | 00.28 |
| Phosphorus (%) | 00.25 | 00.27 |
| Potassium (%) | 00.37 | 00.40 |
| Magnesium (%) | 00.06 | 00.07 |
| Calcium (%) | 00.90 | 00.96 |
| Sodium (%) | 00.50 | 00.53 |
| Iron (ppm) | 66.00 | 70.00 |
| Manganese (ppm) | 09.00 | 10.00 |
| Copper (ppm) | 06.00 | 06.00 |
| Zinc (ppm) | 28.00 | 30.00 |

The individual samples for testing were prepared according to standard procedures. Initially, each 120 mL bottle containing various amounts of food waste and phosphate buffer solution at various pH values was sealed with a septa, heated in an autoclave and then inoculated with 0.5 mL of thermally pretreated sludge from a waste water treatment facility. The food waste material was statistically sampled from the stock of processed food waste to assure homogeneity. The inoculated substrate samples were heated to 95° C. for 15 minutes to inhibit non-spore formers, including methanogens, but not including spore-forming hydrogen-producing microorganisms. The solar collector was used to heat the waste and after hydrogen production. Various combinations of temperature and heating time were considered. It was determined that preprocessing heating at a temperature of 95° C. for 15 minutes was sufficient to eliminate methane production. The initial pH was measured after the bottles were sterilized and prior to inoculation and incubation. Needles for collecting gas samples and measuring pressure were then inserted into each bottle. Continuous monitoring of pressure was accomplished using pressure transducers.

Figure 4:
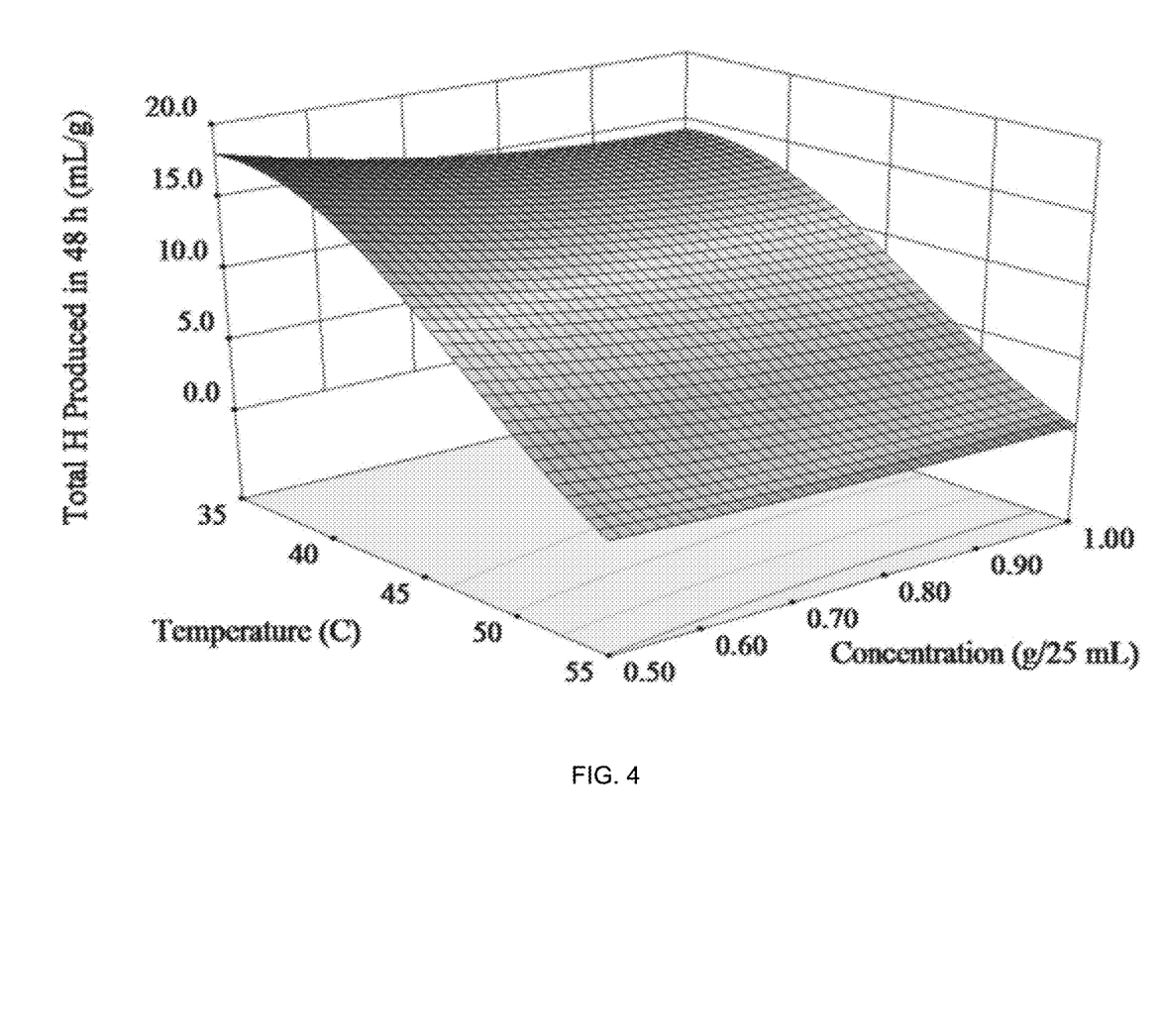
FIG. 4 is a graph illustrating the relationship between hydrogen production from food waste, temperature, and substrate concentration.
Figure 5:
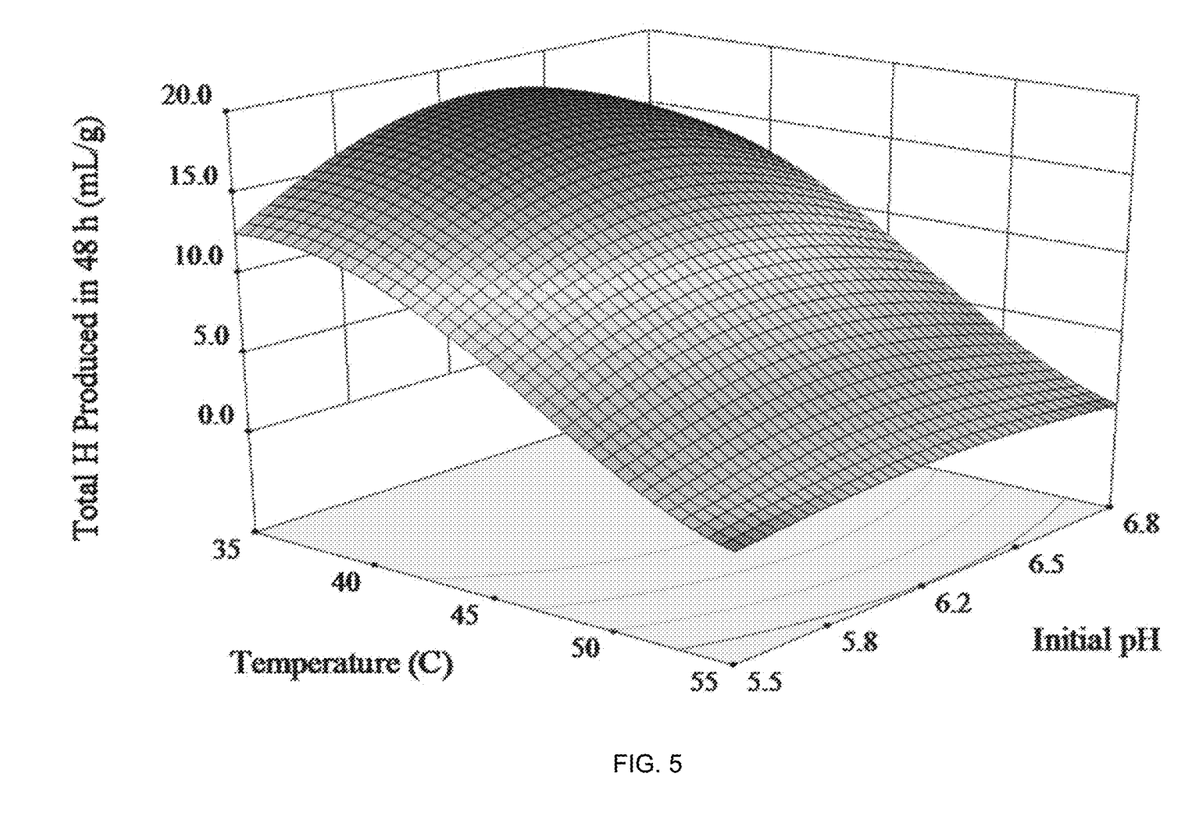
FIG. 5 is a graph illustrating the relationship between hydrogen production from food waste, temperature, and initial pH.

During fermentation, head space pressure in each of the test bottles is continuously monitored and used to calculate the volume of gas produced. The head space gas is sampled automatically for each bottle over time in conjunction with the pressure measurements. Results from the optimization of hydrogen production from food waste using the previously described test apparatus are depicted in FIGS. 4-5. As can be observed in the figures, the choice of operating parameters has direct influence on total hydrogen production from food waste.

Factors that control the hydrogen production rate include temperature, pH, and substrate concentration. Using an iterative approach, it has been possible to determine combinations of these parameters that increase hydrogen production. Increasing substrate concentration allows for a greater use of biomass for a given size of bioreactor, therefore increasing efficiency and practical viability. In some embodiments, the temperature of fermentation of food waste is 35° C.-45° C.

As can be observed in FIG. 4, it is possible to increase hydrogen production rate as substrate concentration is increased. A higher concentration of food waste substrate results in a greater total hydrogen production despite the efficiency of hydrogen production in terms of mL $H_2$ per gram of substrate remaining constant or even decreasing slightly.

As can be observed in FIG. 5, pH also plays a role in hydrogen production. In some embodiments the initial pH for fermentation of food waste is 4.5-6.5. In further embodiments, the initial pH is 5.5-6.5. In certain embodiments, the initial pH is about 6. In some embodiments, the pH is maintained within the initial pH range or substantially at the initial pH value throughout the fermentation process. In some embodiments, sodium hydroxide is used to control pH. In further embodiments, a sodium hydroxide-based additive designed to release over time in response to pH changes may be used as a buffer in the bioreactor. In other embodiments, other buffers or means for controlling pH may be used.

Initial operating parameters for production of hydrogen from DDGS were obtained from tests conducted with the described automated testing device. These tests indicated an increase in hydrogen production from DDGS as compared to food waste. Initial results indicate that yeast remaining in the DDGS after fermentation is able to robustly produce hydrogen under anaerobic conditions. Heat treating of the DDGS as received, prior to hydrogen production, is not required.

Figure 6:
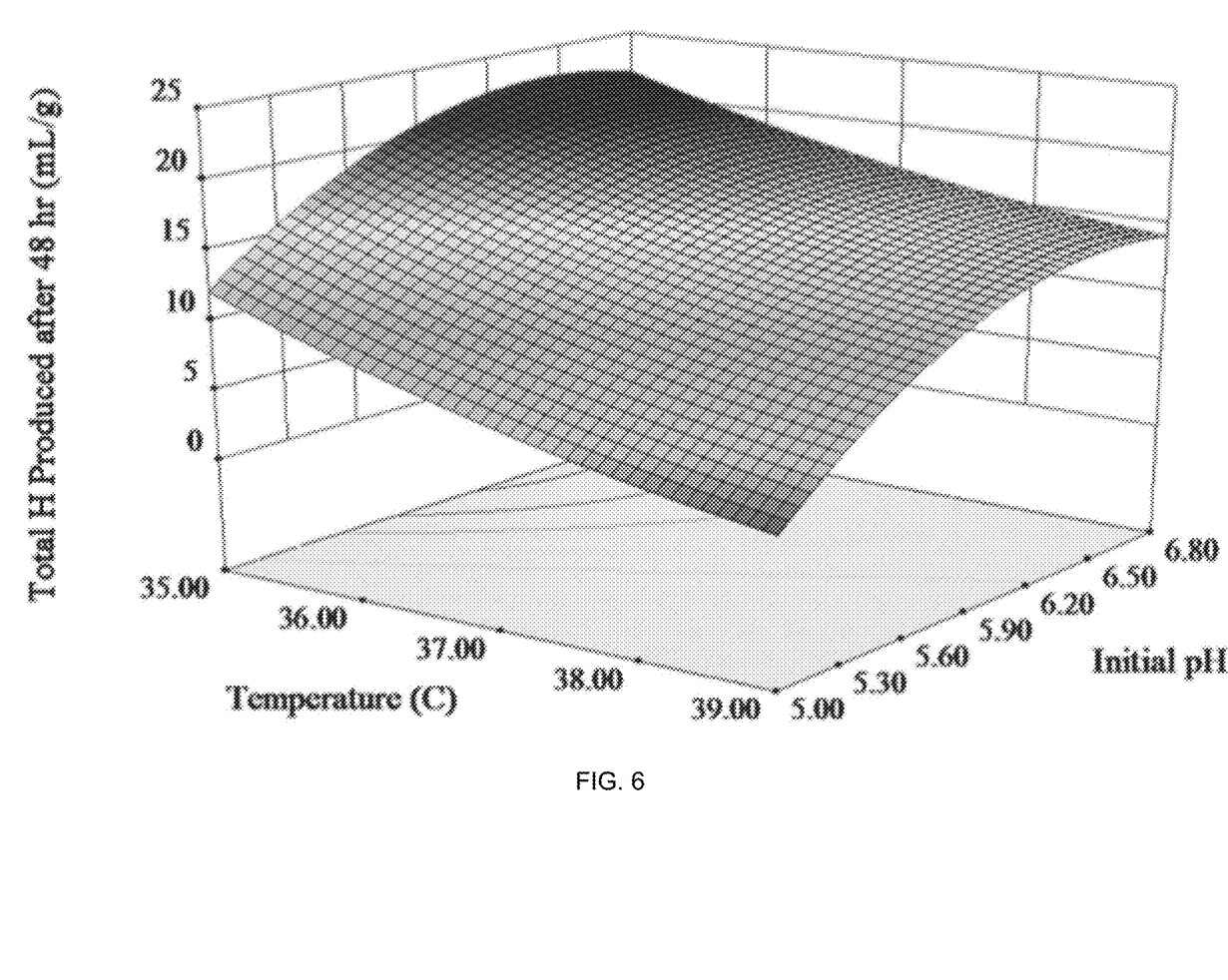
FIG. 6 is a graph the relationship between hydrogen production from DDGS, temperature, and initial pH.
Figure 7:
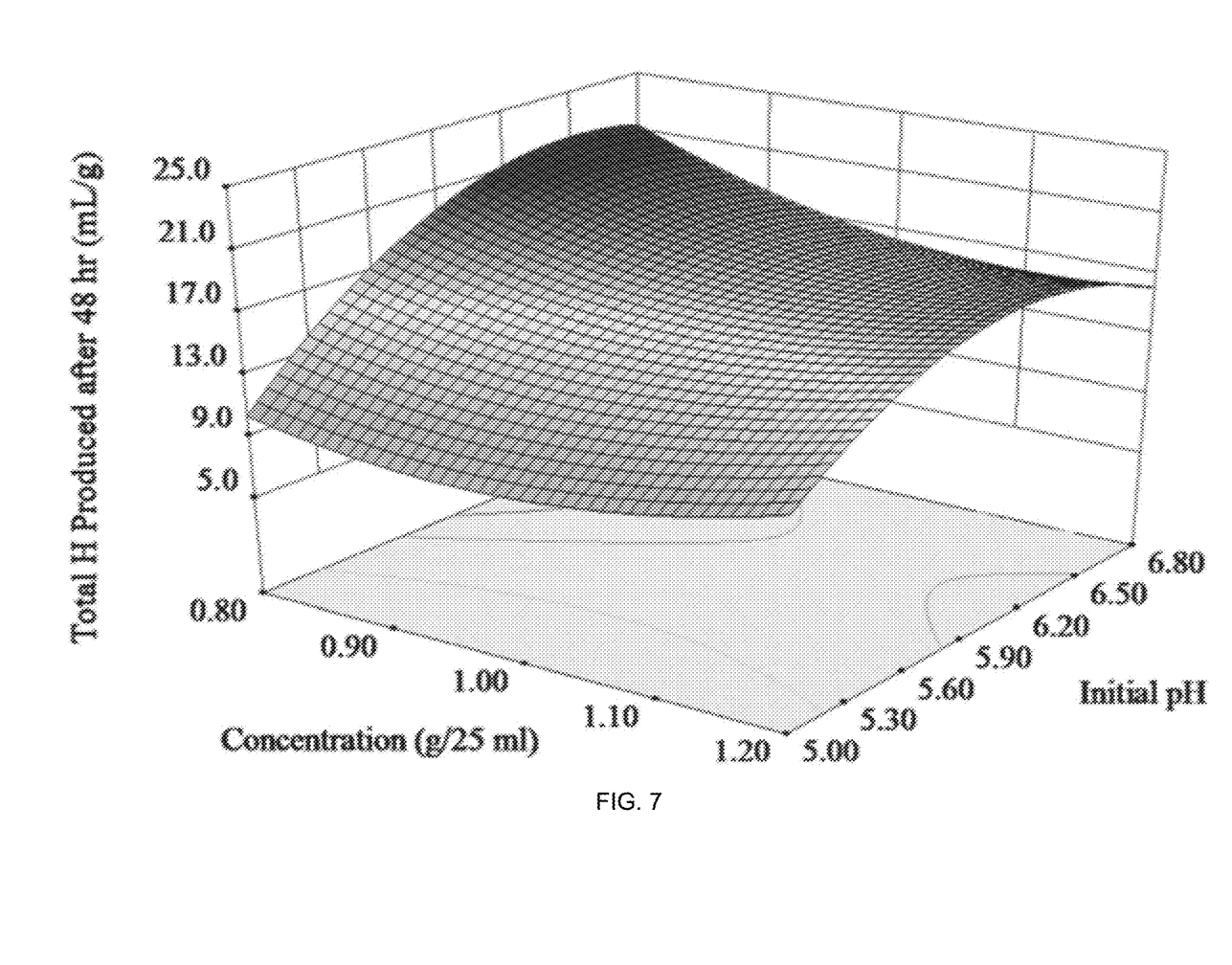
FIG. 7 is a graph illustrating the relationship between hydrogen production from DDGS, substrate concentration, and initial pH.

FIGS. 6-7 show results from experimental data using DDGS as a feedstock in the automated testing device. As can be observed in FIGS. 6-7, the choice of operating parameters has direct influence on total hydrogen production from DDGS. Relevant parameters include temperature, pH, and substrate concentration. Increasing substrate concentration allows for a greater use of biomass for a given size of bioreactor, therefore increasing efficiency and practical viability. As can be observed in FIG. 7, it is feasible to maintain relatively high hydrogen production rates at relatively higher initial pH values as substrate concentration increases.

It has been found that increased hydrogen content is obtained by controlling pH below 6.0. While a relatively high initial pH is indicated as favorable in FIG. 7, maintaining a pH in the range of 4.5-6.5, or in the range of 5-6, or about 5.75, over the duration of fermentation is preferred. At higher pH values increased gas production is observed, but hydrogen concentration decreases slightly. This may be due to the interaction of carbon dioxide concentration and pH. Approximately equal concentrations of hydrogen and carbon dioxide are observed in the head space of the reactor at 48 hours.

To better understand how this process could be used in an industrial setting, tests of hydrogen production from DDGS were performed in a commercial bioreactor (New Brunswick, BioFlo®/CelliGen® 115, 3 L). Hydrogen production levels according to at least one embodiment are approximately 30% greater than for the matrix bottles. This is attributed primarily to continuous stirring. It was also observed that there is less sensitivity to oxygen levels in the bioreactor with DDGS. After an initial small concentration of oxygen in the head space that is believed to be associated with the addition of the DDGS to the system, the dissolved oxygen levels remain at substantially zero throughout the production period.

1 L of water is initially added to the sealed 3 L chamber of the bioreactor. The chamber is then purged with nitrogen to create an anaerobic environment prior to the start of operation. Oxygen levels are monitored with the gas chromatograph during the purge process. DDGS is then added and purging of the bioreactor continues until oxygen levels in the reactor drop to less than less than 0.25% by weight, providing a substantially anaerobic environment. Vessel ports are then sealed and gas production monitoring is started. Temperature, stirring, and pH are automatically controlled and recorded by the control system of the bioreactor during gas production. The flow of gas from the bioreactor is measured with a mass flow meter (Aalborg XFX mass flow meter). The bioreactor is operated at atmospheric pressure. Pressure is continuously measured with a pressure transducer (Omega PX139) and recorded. Gas composition in the reactor head space is determined and recorded every 2 hours with the gas chromatograph.

The bioreactor includes a controller to control temperature and pH within the bioreactor chamber. Based upon preferred values determined from the test matrix, temperature is maintained at 37° C. and pH is maintained at 5.5. Note that the preferred values disclosed by the test matrix and displayed in FIGS. 6-7 are not necessarily the preferred values for use with this small scale bioreactor or larger bioreactors. A 0.75M solution of sodium hydroxide is added by a pump controlled by the bioreactor to maintain the pH at a constant value. As the concentration of the substrate increases, the efficiency and cost effectiveness of the modular energy system increases since the hydrogen produced per unit volume of the bio reactor increases. This allows for decreased mass, size, and cost for the bioreactor.

Figure 8:
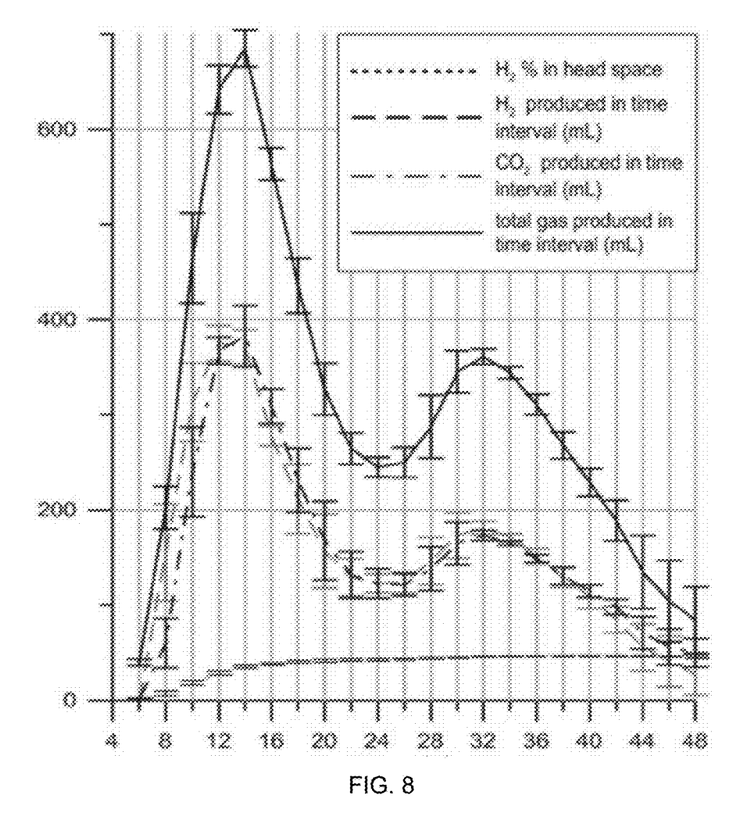
FIG. 8 is a graph illustrating production of hydrogen and carbon dioxide gas over time in a bioreactor.

FIG. 8 depicts measurements of hydrogen and carbon dioxide volumes, and the percentage of hydrogen, present in the bioreactor chamber over time. More particularly, FIG. 8 depicts the gaseous production of 80.0 g of DDGS feedstock in the bioreactor over 48 hours. These values utilize and are correlated with the mass flow rate from the Aalborg mass flow meter. Values for carbon dioxide concentration are calculated and are correlated with pH and production levels, however, $H_2$/g substrate values decreased slightly as substrate concentration increases.

Initial tests indicated unexpected plateaus in the gas production level occurring at approximately 12 hours after addition of the DDGS to the reactor and again at 32 hours. These plateaus have been reduced in size with pH control. Control at constant lower pH values seems to reduce the plateau the most. It is believed that this is attributable to a dual enzyme phenomenon and the equilibrium of carbon dioxide produced through fermentation as a function of pH.

The hydrogen production rate increases with increasing substrate concentration. Concentrations up to 120 g/L were tested. By increasing the agitation it has been possible to decrease the time to first hydrogen production. This decreases production time resulting in reduced system size and cost. Testing efforts have characterized the relation between continuous pH control and production levels for DDGS. In some embodiments, production rates were determined to be 3.0 L of hydrogen from 80.0 g of DDGS in 1 L of buffered demineralized water in 48 hours.

It is anticipated that the parameters determined from the matrix test data and response surface analysis will be used to train a neural network that will then be used to control the bioreactor. Such an approach will be robust and at the same time will be capable of adapting to changes in substrate composition and environmental conditions. Current hydrogen production levels indicate that it is possible to house in a standard shipping container a bioreactor of size sufficient to produce a quantity of hydrogen to supply a reciprocating engine driven generator with an average output of 2 kW. Using the data from FIG. 4, a bioreactor with a chamber length of 8 meters and a diameter of 1.5 meters would produce sufficient hydrogen gas from food waste to power the reciprocating engine-driven generator. The current model assumes a food waste concentration of approximately 5% in the bioreactor. As described previously, there are indications that this concentration can be significantly increased thereby reducing the size of the bioreactor. It should thus be possible to obtain significantly higher hydrogen production levels and consequently dramatically reduce the physical size of the reactor vessel. Alternatively, by using a higher concentration of substrate, a bioreactor of equivalent size could power a higher wattage generator.

One factor in sizing the bioreactor is the concentration of waste material in the bioreactor. Initial tests were performed at a 0.98 mass ratio of water to substrate. Recent optimization efforts have decreased this to 0.75 thereby significantly reducing the size and mass of the bioreactor. Recent test results also indicate that it has been possible to significantly increase the hydrogen production amounts per gram of substrate beyond initial values as a result of the selection of operating parameters, such as temperature and pH.

Preliminary laboratory tests indicate that gas produced by the bioreactor is approximately 25% hydrogen with the remainder being nitrogen and carbon dioxide. Hydrogen gas can be separated from a gas stream using various methods known in the art. Hydrogen separation using zeolites and membrane technology has been shown to improve hydrogen yields in dark fermentation systems. Organometallic reagents and catalysts in ionic liquids may also be used to remove carbon dioxide from the gas stream. In some embodiments, the modular energy system includes a gas separator component for hydrogen separation and purification so that purified hydrogen will be available for use in a fuel cell or heat engine to produce electricity locally.

In some embodiments, hydrogen is stored in the bioreactor by increasing pressure within the bioreactor chamber. This could provide a means of providing limited peaking capability. However, observations have indicated that hydrogen production levels tend to decrease as pressure increases, so in-chamber storage may be inconsistent with maximal hydrogen production.

Figure 9:
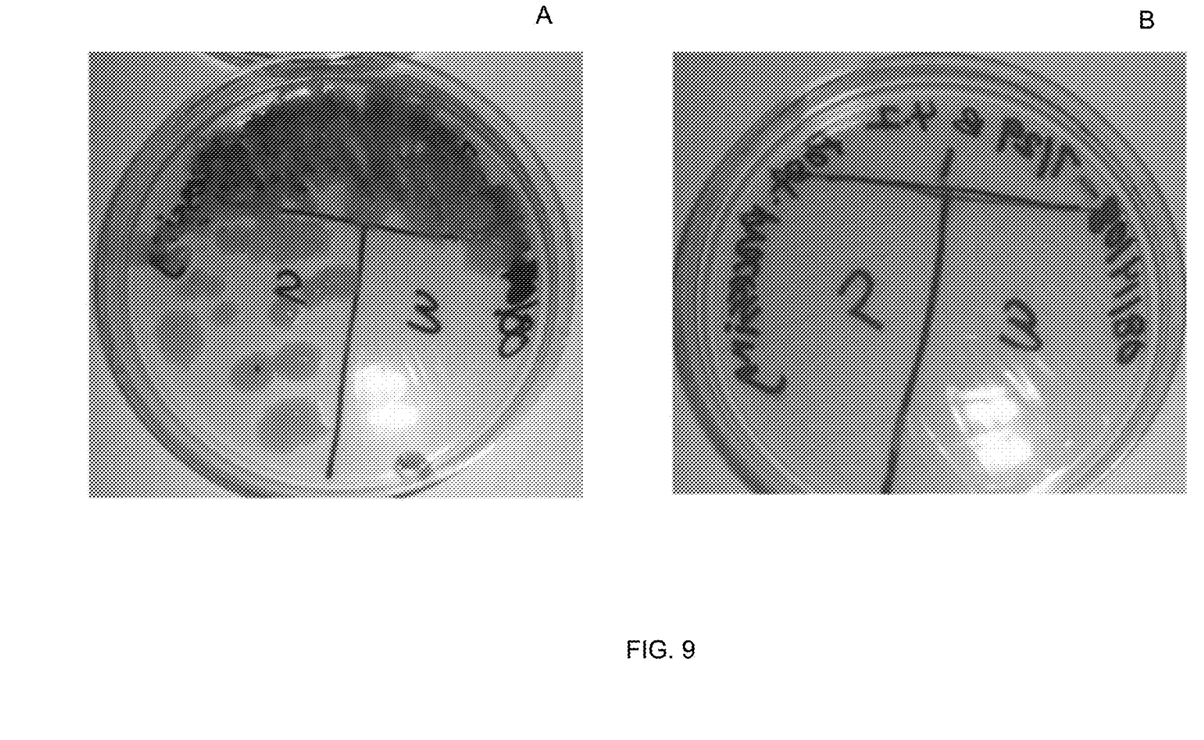
FIG. 9 is a pair of photographs showing Petri plates treated with (A) organic waste and (B) heat-treated organic waste.

This modular energy system will be particularly useful in remote and disaster situations by producing electricity, heat, sanitized fertilizer and potable water, as well as reducing environmental contamination of water and food resources by untreated organic waste. After the organic waste material has produced hydrogen in the bioreactor, it is removed and heated to sanitize it for use as fertilizer. By heating it is possible to eliminate the majority of potentially harmful organisms left in the digested material. To experimentally verify this, substrate was removed from several bottles after hydrogen production and was plated on a standard nutrient Petri plate and then incubated for 48 hours at 60° C. As shown in FIG. 9(A), this plate shows growth of organisms remaining in the digested waste. The same bottles were then heated to 95° C. for 30 minutes using heat energy from the solar collector. Samples of the heat treated digested waste were plated onto the same type of nutrient plates used previously. As shown in FIG. 9(B), the post-processing heat treated waste show no growth.

The heat-treatment processing of waste material depends on the availability of heat from the solar thermal system which depends on the availability and intensity of sunlight. In addition to variation through the day, the output from the solar thermal system also depends on factors such as the time of the year, weather, and geographic location. The availability of solar energy influences the system energy balance and hence the amount of energy available for ancillary purposes such as production of potable water. Heat energy stored in the thermal storage unit is available to reduce the effect of times when there is little or no sun light. The production of hydrogen from the bioreactor itself is influenced to a lesser degree by variations in sunlight since it is anticipated that the residency time for the waste material in the reactor will be on the order of 48 hours and it is possible to store quantities of preprocessed waste material prior to introduction into the bioreactor itself. Varying the pressure in the bioreactor as described previously also reduces the influence of solar energy variations when considering the energy balance for the modular energy system.

The developed process provides a means of using DDGS to produce hydrogen and thereby add additional value to ethanol production. It is anticipated that the produced hydrogen could be used at the ethanol plant directly as an energy source either directly for heat production, as fuel for a heat engine, such as reciprocating or turbine electric generator, or as a process enhancement to drive other industries processes which require hydrogen.

The high heating value of ethanol is 12,830 BTU/lb and for hydrogen is 59,806 BTU/lb. The conversion rate for corn to ethanol is approximately 2.60 gal/bushel, with one gallon of ethanol having a high heating value of 83,961 BTU per gallon. One tonne (1000 kg) of corn produces approximately 378 L of ethanol and 309 kg of DDGS.

For the DDGS hydrogen production process disclosed herein, 37.5 mL of hydrogen at STP is produced in 48 hours per gram of substrate feedstock in the bioreactor. For comparison purposes, it can be assumed that the hydrogen produced from the DDGS is combusted with high heating value to produce heat. This results in a 14% increase in the heat produced by the combustion of hydrogen and ethanol from grain as compared to the combustion of ethanol alone. By using DDGS left over from bioethanol production to produce biohydrogen, the total amount of renewable energy created from a given amount of grain is increased. Other uses for the produced hydrogen have the potential to further increase the efficiency improvement. It is anticipated that the infrastructure associated with the production of DDGS will be relatively small in comparison with total plant cost and hence it can be assumed that this process has the potential to increase ethanol efficiency by at least 10%.

While the inventions have been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A modular renewable energy system comprising:
 a solar collector system for generating heat energy;
 a bioreactor including a chamber for fermenting organic waste; and
 one of a fuel cell and a heat engine in gaseous communication with the bioreactor;

wherein anaerobic fermentation of organic waste in the chamber generates hydrogen gas, the hydrogen gas being directed to the one of a fuel cell and a heat engine; and wherein heat energy effective for sterilization is applied to the organic waste subsequent to fermentation, the heat energy being generated by the solar collector system.

2. The modular renewable energy system of claim 1, further comprising a housing having an interior and an exterior, wherein the bioreactor is located in the interior of the housing, the one of a fuel cell and a heat engine is located in the interior of the housing, and the solar collector system is located on the exterior of the housing.

3. The modular renewable energy system of claim 1, wherein heat energy effective to substantially inactivate methane-producing microorganisms is applied to the organic waste prior to fermentation, the heat energy being generated by the solar collector system.

4. The modular renewable energy system of claim 1, further comprising an apparatus for distilling water using heat energy generated by the solar collector system.

5. The modular renewable energy system of claim 1, further comprising a controller for controlling the temperature and pH within the bioreactor chamber.

6. The modular renewable energy system of claim 1, wherein the heat engine combusts the hydrogen in a cylinder to drive a piston.

7. The modular renewable energy system of claim 1, wherein the heat engine combusts the hydrogen in the combustor of a gas turbine.

8. The modular renewable energy system of claim 1, wherein the one of a fuel cell and a heat engine is connected to the bioreactor.

9. The modular renewable energy system of claim 1, wherein the solar collector system is connected to the bioreactor.

10. The modular renewable energy system of claim 1, further comprising a gas conditioner for separating hydrogen from other gases, wherein hydrogen is directed to the gas conditioner prior to being directed to the one of a fuel cell and a heat engine.

11. A modular renewable energy system comprising:
a bioreactor including a chamber for fermenting organic waste; and
one of a fuel cell and a heat engine in gaseous communication with the bioreactor;
wherein anaerobic fermentation of organic waste in the chamber generates hydrogen gas, the hydrogen gas being directed to the one of a fuel cell and a heat engine; and
wherein heat energy effective for sterilization is applied to the organic waste subsequent to fermentation.

12. The modular renewable energy system of claim 11, further comprising a solar collector system for generating heat energy, wherein the heat energy effective for sterilization applied to the organic waste subsequent to fermentation is generated by the solar collector system.

13. The modular renewable energy system of claim 12, further comprising a housing having an interior and an exterior, wherein the bioreactor is located in the interior of the housing, the one of a fuel cell and a heat engine is located in the interior of the housing, and the solar collector system is located on the exterior of the housing.

14. A modular renewable energy system comprising:
a solar collector system for generating heat energy;
a bioreactor including a chamber for fermenting organic waste; and
a post-processing unit in liquid communication with the bioreactor;
wherein heat energy effective for sterilization is applied to the organic waste in the post-processing unit subsequent to fermentation of the organic waste in the chamber.

15. The modular renewable energy system of claim 14, further comprising one of a fuel cell and a heat engine in gaseous communication with the bioreactor, wherein anaerobic fermentation of organic waste in the chamber generates hydrogen gas, the hydrogen gas being directed to the one of a fuel cell and a heat engine.

* * * * *